US012465677B2

(12) United States Patent
Schwarz et al.

(10) Patent No.: US 12,465,677 B2
(45) Date of Patent: Nov. 11, 2025

(54) MEDICAL FLUID PUMP WITH A CARRYING HANDLE AND SUPPORTING OR HOLDING DEVICE FOR A MEDICAL FLUID PUMP

(71) Applicant: B. Braun Melsungen AG, Melsungen (DE)

(72) Inventors: Jan Schwarz, Melsungen (DE); Matthias Schwalm, Schwalmstadt (DE); Marcel Stich, Nieste (DE); Peter Heine, Landsberied (DE); Christoph Erlen, Kassel (DE); Joachim Schuetz, Fulda (DE); Michael Rauscher, Muenchwilen (CH)

(73) Assignee: B. Braun Melsungen AG, Melsungen (DE)

( * ) Notice: Subject to any disclaimer, the term of this patent is extended or adjusted under 35 U.S.C. 154(b) by 551 days.

(21) Appl. No.: 17/854,021

(22) Filed: Jun. 30, 2022

(65) Prior Publication Data

US 2023/0001074 A1 Jan. 5, 2023

(30) Foreign Application Priority Data

Jul. 1, 2021 (DE) ..................... 20 2021 103 514.5

(51) Int. Cl.
*A61M 5/14* (2006.01)

(52) U.S. Cl.
CPC ................................ *A61M 5/1415* (2013.01)

(58) Field of Classification Search
CPC .............. A61M 5/1415; A61M 5/1452; A61M 5/1408; A61M 5/1413; A61M 5/14244
See application file for complete search history.

(56) References Cited

U.S. PATENT DOCUMENTS

| | | | | |
|---|---|---|---|---|
| 368,053 A * | 8/1887 | Berger | B65D 25/2841 | 16/445 |
| 5,154,499 A * | 10/1992 | Atkinson | A61M 5/1415 | 403/91 |
| 2012/0025492 A1* | 2/2012 | Grintz | B62B 7/08 | 280/647 |

FOREIGN PATENT DOCUMENTS

| | | | |
|---|---|---|---|
| CN | 102266599 A | | 12/2011 |
| CN | 102266599 B | * | 7/2013 |
| CN | 203634569 U | | 6/2014 |
| DE | 102017122044 | * | 3/2019 |
| DE | 102017122044 A1 | * | 3/2019 |
| EP | 2700424 A1 | | 2/2014 |

OTHER PUBLICATIONS

Search Report received in German Application No. 20 2021 103 514.5 dated May 5, 2022, with translation, 7 pages.

* cited by examiner

*Primary Examiner* — Rebecca E Eisenberg
*Assistant Examiner* — Matthew Wrubleski
(74) *Attorney, Agent, or Firm* — Christopher A. Rothe; CM Law

(57) ABSTRACT

A medical fluid pump has a housing, a front lid pivotably hinged to the housing, and a carrying handle. The carrying handle, which may have a bow-shaped design, is pivotably hinged to two opposing side faces of the housing. The carrying handle is hinged to the housing such that a handle portion of the carrying handle lies, in a swiveled-out state, in a direction of gravity substantially over a center of gravity of the fluid pump.

20 Claims, 5 Drawing Sheets

MEDICAL FLUID PUMP WITH A CARRYING HANDLE AND SUPPORTING OR HOLDING DEVICE FOR A MEDICAL FLUID PUMP

CROSS-REFERENCE TO RELATED APPLICATION

This application claims priority under 35 U.S.C. § 119 to German Application No. 20 2021 103 514.5, filed Jul. 1, 2021, the content of which is incorporated by reference herein in its entirety.

FIELD

The disclosure relates to a medical fluid pump with a cuboid pump housing, a front lid pivotably hinged to the housing, and a carrying handle, especially of bow-shaped design, pivotably hinged to two opposing side faces of the housing.

BACKGROUND

The development in modern medicine, especially in intensive-care medicine, has led to infusion therapies requiring the specific use and the exact dosing of highly efficient drugs. In the scope of these therapies, depending on the clinical picture, often a plurality of drugs and optionally parenteral feeding must be administered. Thus, there is a need of modular infusion devices adapted to be easily equipped with a plurality of fluid pumps/infusion pumps. For this purpose it is common to arrange the infusion pumps (but also syringe pumps) as a group during use in or at or by means of a supporting or holding device so as to ensure an intended operation and an intended use of the pumps.

The fluid pumps usually comprise a carrying handle for transport and for improving their handling. Thus, for instance, EP 2 700 424 A1 illustrates an infusion pump with a handlebar or carrying handle which is fastened immovably to a housing of the infusion pump.

Further, CN 1 02 266 599 A1 discloses an infusion pump having a pivotable carrying handle hinged thereto at the middle of its upper side. In a swiveled-in/folded-in position the carrying handle is received in a recess.

Moreover, also CN 2 03 634 569 U illustrates a further medical fluid pump with a pump housing and a carrying handle pivotably hinged thereto. The known fluid pumps, however, tend to tilt when they are carried by the carrying handle in a swiveled-out/folded-out position.

SUMMARY

Objects and aims of the invention are to remedy or at least mitigate the disadvantages of the state of the art and to provide in particular a medical fluid pump with a carrying handle which guarantees a horizontal orientation of the fluid pump when the fluid pump is carried by the carrying handle. A horizontal orientation of the fluid pump means that the fluid pump does not tilt even after being lifted by the carrying handle.

In accordance with the disclosure the medical fluid pump is configured/adapted such that the carrying handle is hinged to the housing such that a handle portion/handle region of the carrying handle lies, in a swiveled-out state, in the direction of gravity (substantially) over a center of gravity of the fluid pump.

Thus, it may be ensured that the fluid pump does not tilt or does only tilt slightly/negligibly when lifted by the gripping handle.

In accordance with the disclosure, the medical fluid pump may be designed as an infusion/peristaltic pump or as a perfusion/syringe pump.

In a preferred design, the carrying handle may, in the swiveled-out state, be arranged substantially perpendicular to a lid or top face of the housing, and, in a swiveled-in state, be oriented substantially parallel to the lid face. Thus, good gripping ability of the handle portion in the swiveled-out state and a space-saving accommodation of the handle portion at the fluid pump in the swiveled-in state may be guaranteed.

In a particularly preferred manner the carrying handle may be hinged to a housing upper shell of the pump housing. This means that the pump housing preferably comprises at least a housing lower part and a housing upper shell, wherein the carrying handle is hinged to the housing upper shell.

Moreover, it is of advantage if the carrying handle, in the swiveled-in state, projects/protrudes at least partially over a rear side/rear face of the housing. Thus, the carrying handle is easier to grip in the swiveled-in state since—if at all—merely a part of the handle portion is covered by the housing.

In accordance with an advantageous further development the medical fluid pump may further comprise a spring element whose spring force/prestressing force counteracts a weight of the carrying handle so as to push the carrying handle to the swiveled-out state, which facilitates the swiveling-out/folding-out of the carrying handle since a user only has to overcome a part of the weight of the carrying handle. In other words, the user is supported by the spring element when folding out the carrying handle.

Furthermore, it may be expedient if the carrying handle comprises first locking means which, preferably by outputting an acoustic signal, especially a clicking noise, interlocks with second locking means arranged at the housing. The first locking means may interlock with the second locking means in the swiveled-in state and the swiveled-out state. Moreover, it is also of particular advantage if the first locking means is a spring-loaded disk with two grooves formed thereon, in which a rib arranged at the housing engages as a second locking means. The locking means ensure that the carrying handle is kept in the desired position, i.e., in the swiveled-in or the swiveled-out state. By the output of an acoustic signal the user moreover obtains feedback as to whether and/or when the carrying handle is swiveled-out and/or swiveled-in completely.

In accordance with a further advantageous design the carrying handle may comprise at least one damping element, preferably in the form of a plastic element received in a blind hole of the carrying handle, which rests on the housing in the swiveled-in state. Thus, it may be prevented that the carrying handle hits the pump housing during swiveling-in/folding-in.

Moreover, the fluid pump in accordance with the disclosure may, in a preferred further development, comprise a coupling structure for connecting the medical fluid pump with a further medical fluid pump. Moreover, it may be of advantage if the carrying handle of the medical fluid pump is adapted to carry a plurality of, especially three, medical fluid pumps connected with each other.

Furthermore, the disclosure relates to a supporting or holding device for the (position-safe) holding of at least one medical fluid pump in accordance with the disclosure during operation thereof, with a preferably columnar basic or main body, from the one side face of which a plurality of trays project which are each adapted to hold a pump in an operating position, wherein a carrying handle receiving recess or concavity receiving a carrying handle of the respective fluid pump is formed in the basic body for each tray.

Moreover, the disclosure relates to a supporting or holding system comprising

- at least one medical fluid pump in accordance with the disclosure, and
- a supporting or holding device in accordance with the disclosure with at least one tray provided to hold the fluid pump in an operating position.

BRIEF DESCRIPTION OF THE DRAWING FIGURES

In the following, the disclosure will be explained by means of a preferred embodiment with the aid of Figures, of which:

The Figures are of schematic nature and serve merely for the understanding of the disclosure. Equal elements are provided with the same reference numbers.

DETAILED DESCRIPTION

Figure 1:
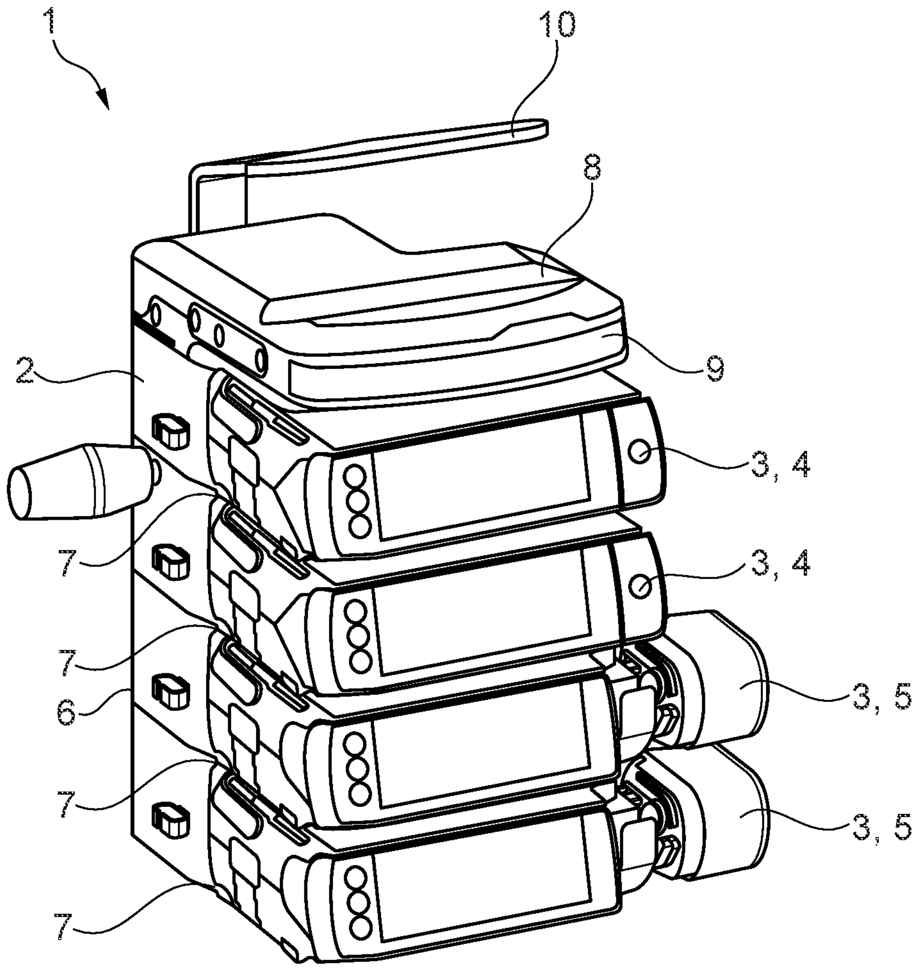
FIG. 1 is a perspective view of a supporting or holding system in accordance with the disclosure according to a preferred embodiment.

FIG. 1 shows a supporting or holding system 1 in accordance with the disclosure with a substantially columnar supporting or holding device 2 (in the following called rack) and four medical fluid pumps 3 received in the rack 2. As is shown by way of example in FIG. 1, every two infusion pumps/peristaltic pumps/tube pumps 4 and two perfusion pumps/syringe pumps 5 are arranged in the rack 2.

The rack has a basic body 6 extending in a vertical and/or column longitudinal direction, at which the fluid pumps 3 are arranged one above the other. The fluid pumps 3 are arranged such that rear sides of the fluid pump 3 abut on a front side of the basic body 6 and/or are positioned at a small distance thereto. As explained in detail in the following, four trays 7 for receiving a respective fluid pump 3 project from the basic body 6 at the front side of the basic body 6. The trays 7 are designed as substantially rectangular plates. Furthermore, the rack 2 comprises, at a front face of the basic body 6, a cover 8. The rack side to which the cover 8 is fastened is the top side of the rack 2. The cover 8 is connectable to the basic body 6 and comprises an output unit 9 for the output of acoustic and visual alarm signals. Moreover, the rack 2 has a carrying handle 10 fastened to a rear side of the basic body 6 which faces away from the trays 7. By means of the carrying handle 10 the supporting or holding system 1, i.e. the rack 2 along with the fluid pumps arranged therein, may be carried.

Figure 2:
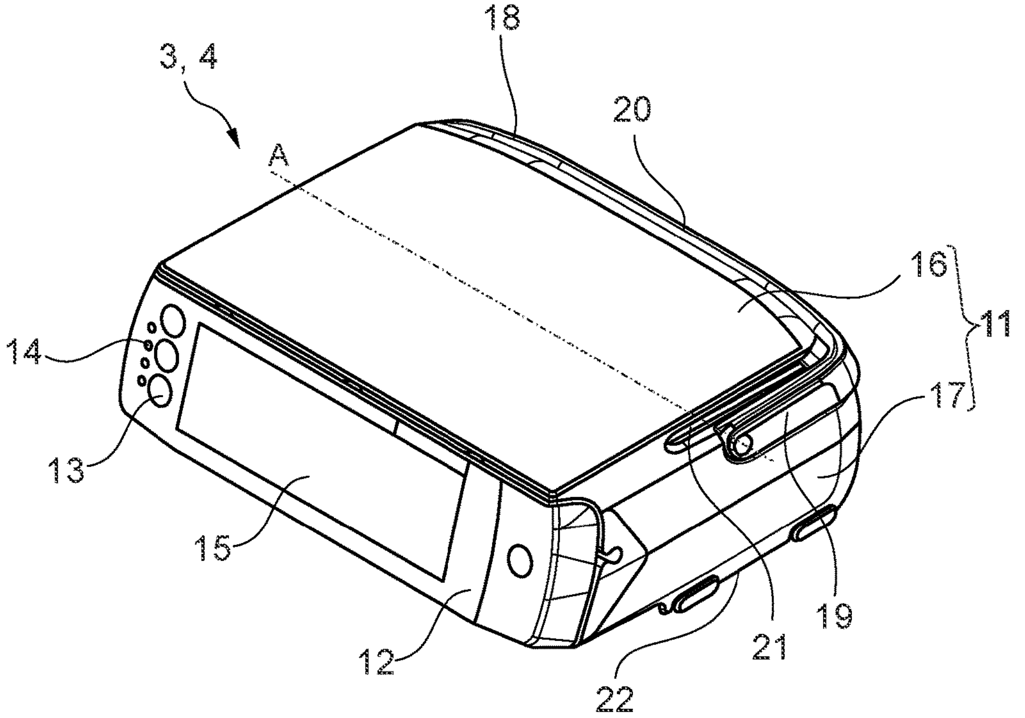
FIG. 2 is a perspective view of a medical fluid pump in accordance with the disclosure according to the preferred embodiment.

In FIG. 2 the medical fluid pump 3 in accordance with the preferred embodiment is shown. The medical fluid pump 3 illustrated in FIG. 2 is designed as an infusion pump 4. It is to be understood that the medical fluid pump 3 in accordance with the disclosure may also be designed as a syringe pump 5. As illustrated in FIG. 2, the fluid pump 3 comprises a substantially cuboid pump housing 11 to the front side of which, i.e., in the installed state to the side facing away from the rack 2, a front lid 12 is pivotably hinged. A plurality of operating keys 13, a plurality of signal lights 14, and a touch display 15 are arranged on a front side of the front lid 12.

The pump housing 11 further comprises a housing upper shell 16 and a housing lower part/housing lower shell 17 which are preferably adapted to be detachably connected with each other and thus form the pump housing 11. A carrying handle 18 formed as a U-shaped handle bracket is pivotably hinged to the housing upper shell 16. The carrying handle 18 encompasses the housing upper shell 16 in a width direction of the fluid pump 3 and/or a front lid longitudinal direction, so that the carrying handle 18 is hinged to both side faces of the housing upper shell 16 and/or the pump housing 11. In other words, the carrying handle 18 has two fastening struts 19 hinged to the side faces of the housing upper shell 16 and a handle portion/handle region 20 formed there between.

Figure 3:
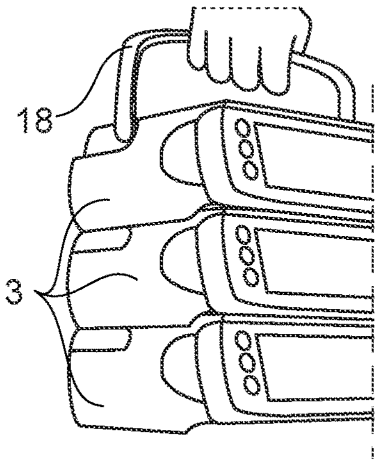
FIG. 3 is perspective partial view of a group of a plurality of medical fluid pumps in accordance with the preferred embodiment.

As illustrated in FIG. 3, in accordance with the preferred embodiment three medical fluid pumps 3 may be stacked one upon the other, be connected/coupled with each other directly (i.e. without the use of a rack), and then be carried with the carrying handle 18 of the uppermost fluid pump 3. This means that the carrying handle 18 of the/each medical fluid pump 3 is adapted and dimensioned to carry a (direct) group of three fluid pumps 3 coupled with one another. In order to couple the fluid pump 3 with a further fluid pump 3, the fluid pump 3 comprises a coupling structure in the form of a skid-rail-system. For this purpose, the/each fluid pump 3 has on its upper side/lid face, i.e. at the housing upper shell 16, rails extending on both sides in the depth direction. At the lower side and/or at the housing lower shell 17 the fluid pump 3 furthermore comprises skids 22 extending on both sides in the depth direction. If, now, the fluid pump 3 is to be coupled with a further fluid pump 3, the skids 22 of the one fluid pump 3 engage in the rails 21 of the further fluid pump 3 and are guided in them. Now, the two fluid pumps 3 are shifted against each other in the depth direction until a locking mechanism (not illustrated in detail here) interlocks and/or fixes the two fluid pumps 3 with/to each other.

Figure 4:
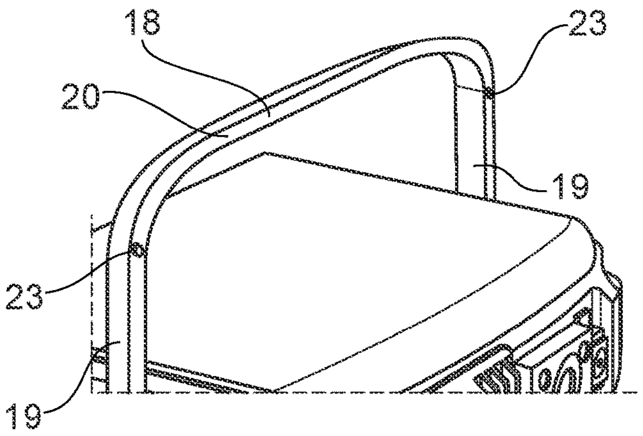
FIG. 4 is a perspective partial view of the medical fluid pump in accordance with the disclosure according to the preferred embodiment.
Figure 5:
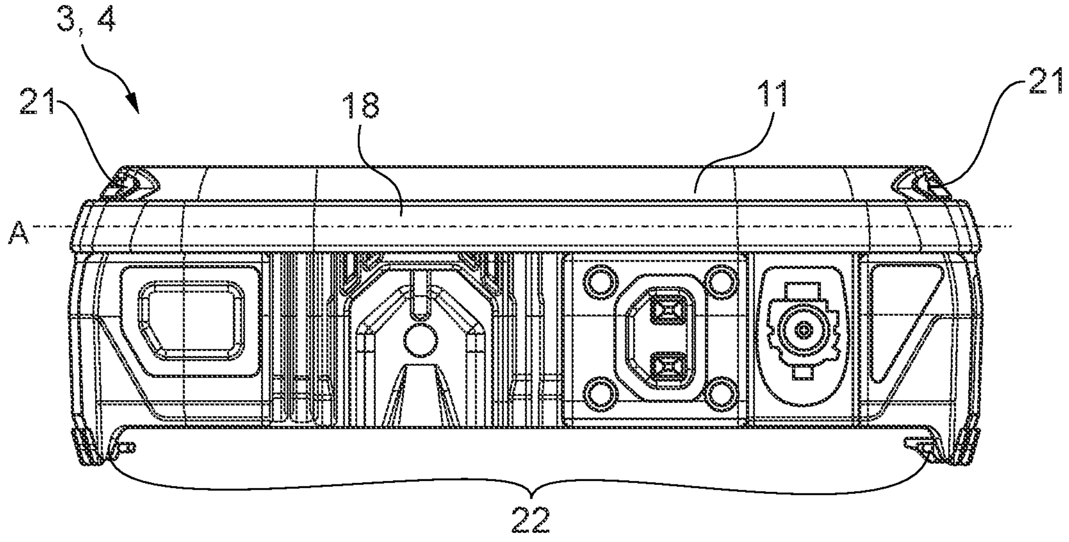
FIG. 5 is a rear view of the medical fluid pump in accordance with the disclosure according to the preferred embodiment.
Figure 6:
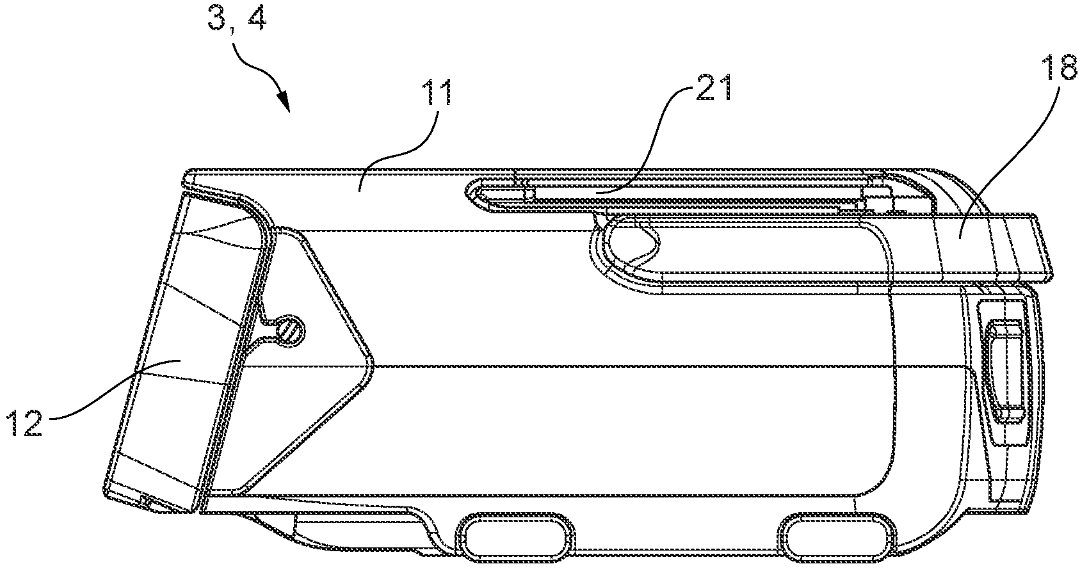
FIG. 6 is a side view of the medical fluid pump in accordance with the disclosure according to the preferred embodiment.

In FIG. 4, the fluid pump 3 in accordance with the preferred embodiment is illustrated with a swiveled-out/folded-out carrying handle 18. In the swiveled-out state the carrying handle 18, i.e. the fastening struts 19, is positioned substantially perpendicular to the lid face of the housing upper shell 16. As may be recognized in FIGS. 5 and 6, the carrying handle 18 extends in the folded-in state substantially parallel to the lid face. A swivel axis A of the carrying handle 18, i.e. the axis extending through the two pivot points of the fastening struts 19, is arranged in the height direction of the pump housing 11 in an upper end portion of the housing upper shell 16, so that the carrying handle 18 does not project over the pump housing 11 in the height direction in the folded-in state. Moreover, the swivel axis A of the carrying handle 18 is arranged in the depth direction of the pump housing 11 such that the carrying handle 18 projects over a rear side of the pump housing 11 in the folded-in state (see FIGS. 5 and 6). Thus, it is easier to grip the carrying handle 18 in the folded-in state and to fold it out. This means that the handle portion 20 of the carrying handle 18 is, in the folded-in state, only covered partially by the pump housing 11 in a view from the bottom on the pump housing 11, so that a partial region of the handle portion 20 remains permanently grippable. Moreover, the swivel axis A of the carrying handle 18 is, as explained in detail in the following, arranged at the pump housing 11, i.e., the carrying handle 18 is hinged to the housing upper shell 16, such that the handle portion 20 of the carrying handle 18 lies, in the folded-out state, in a direction of gravity (substantially) over the center of gravity of the fluid pump 3 and tilting of the fluid pump 3 may be prevented and/or tilting is negligibly slight.

As is illustrated in FIG. 4, damping elements 23 are arranged at an underside/bottom side of the carrying handle 18, i.e., at a side opposing the pump housing 11 in the height direction in the folded-in state. These damping elements are, in the preferred embodiment, designed as plastic elements and are received in appropriate blind holes 24 (covered by the damping elements 23 in FIG. 4) in the carrying handle 18. In the folded-in state the damping elements 23 are in contact with the pump housing 11, i.e., the carrying handle 18 rests on the pump housing 11 in the folded-in state via the damping elements 23.

Figure 7:
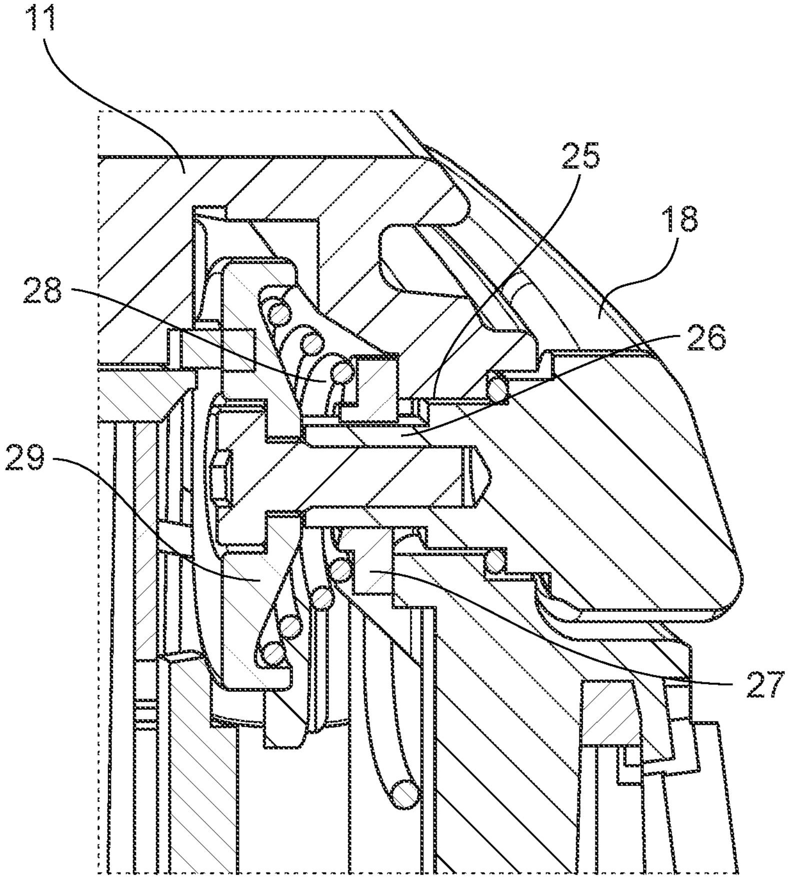
FIG. 7 is a partial sectional view of a carrying handle hinge mechanism of the medical fluid pump in accordance with the disclosure according to the preferred embodiment.
Figure 8:
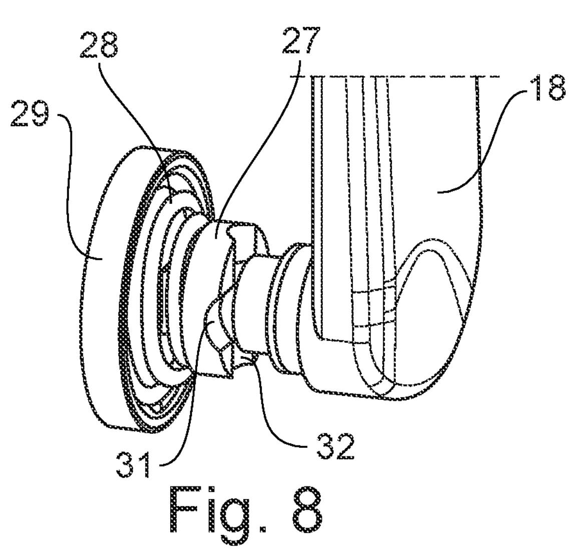
FIG. 8 is a perspective partial view of a catching means of a carrying handle of the medical fluid pump in accordance with the disclosure according to the preferred embodiment.

FIG. 7 is a partial view of a sectional representation of the medical fluid pump 3, wherein the intersecting plane is spanned through the vertical axis and the swivel axis A. FIG. 7 illustrates a hinge mechanism by which the carrying handle 18 is fixed to the pump housing 11 in one of the two pivot points. For this purpose, the carrying handle 18 comprises a fastening pin 26 projecting from an inner side of the fastening strut 19 and passing through a through-hole 25 in the pump housing 11. This means that the fastening pin 26 passes through the through-hole 25 to an inner side of the pump housing 11. At the inner side of the pump housing 11, as illustrated in FIG. 8, a groove disk 27 and a spring element 28 are arranged and supported on the fastening pin 26. The groove disk 27 is coupled in a torque-proof manner with the fastening pin 26, so that the groove disk 27 rotates with the fastening pin 26 when the carrying handle 18 is swiveled from the folded-in state to the folded-out state and/or from the folded-out state to the folded-in state. Moreover, a counter plate 29 is screwed with the fastening pin 26 such that the spring element 28 biases the groove disk 27 against and/or pushes it away from the counter plate 29. In other words, in an axial direction of the fastening pin 26, the groove disk 27, the spring element 28, and the counter plate 29 are arranged on or at the fastening pin 26 in this order.

Figure 9:
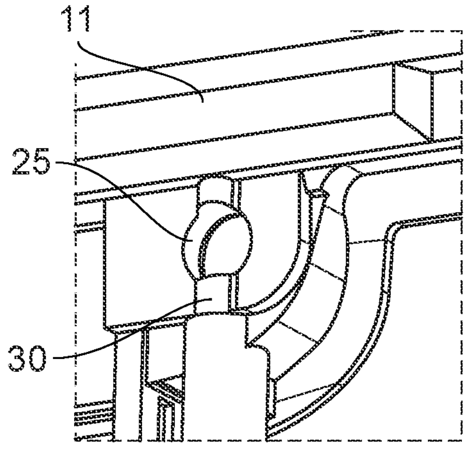
FIG. 9 is a perspective partial view of a catching means of a pump housing of the medical fluid pump in accordance with the disclosure according to the preferred embodiment.

Furthermore, as may be recognized in FIG. 9, a rib 30 is formed in the region of the through-hole 25 at the pump housing 11 on the inner side of the pump housing 11. It extends in the preferred embodiment substantially in a height direction of the pump housing 11. At the groove disk, in turn, a first groove 31 and a second groove 32 are formed, wherein the first groove 31 and the second groove 32 are oriented at a defined angle to each other. In the preferred embodiment this angle is approx. 90°, i.e., the first groove 31 and the second groove 32 are substantially orthogonal/perpendicular to each other.

When the carrying handle 18, as illustrated in FIG. 7, is in the folded-in state, the spring element 28 presses the groove disk 27 against the pump housing 11 such that the first groove 31 encompasses the rib 30. In other words, the groove disk 27, especially the first groove 31 of the groove disk 27, interlocks in the folded-in state of the carrying handle 18 with the rib 30 of the pump housing 11 such that the carrying handle 18 is thereby fixed to the pump housing 11. If, now, the carrying handle 18 is swiveled from the folded-in state to the folded-out state, an additional force has to be exerted first of all so as to release the locking between the first groove 31 and the rib 30. After the releasing of the locking, the fastening pin 26 and hence, as mentioned before, the groove disk 27 rotates relative to the pump housing 11 until the rib 30 finally locks with the second groove 32 of the groove disk 27. This means, the carrying handle 18 is held in the folded-out state by the locking between the rib 30 and the second groove 32. The second groove 32 is oriented at the groove disk 27 such that the handle portion 20 of the carrying handle is, in the folded-out state, arranged in a gravity direction above/over the center of gravity of the fluid pump 3, so that tilting of the fluid pump 3 during lifting of the fluid pump 3 by the carrying handle 18 can be prevented.

In the preferred embodiment the groove disk 27 thus serves as a first locking means of the carrying handle 18 and the rib 30 as a second locking means of the pump housing 11. When the groove disk 27, as explained before, locks with the rib 30, i.e., when the rib 30 engages in the first groove 31 and/or in the second groove 32, the fluid pump 3 outputs an acoustic signal in the form of a clicking noise, which indicates and/or ensures a proper locking of the carrying handle 18 to the user.

As explained before, the spring element 28 biases the groove disk 27 against the counter plate 29 so as to press the groove disk 27 against the pump housing 11. Additionally, however, the spring element 28 may also fulfil the function of a torsion spring so as to support the user when swiveling the carrying handle 18 from the folded-in state to the folded-out state. In other words, the spring element 8 is designed as a pressure and torsion spring, wherein the spring force amount of the torsion spring counteracts gravity and thus pushes the carrying handle 18 to the folded-out state. Thus, the handling of the carrying handle 18 can be improved substantially.

Figure 10:
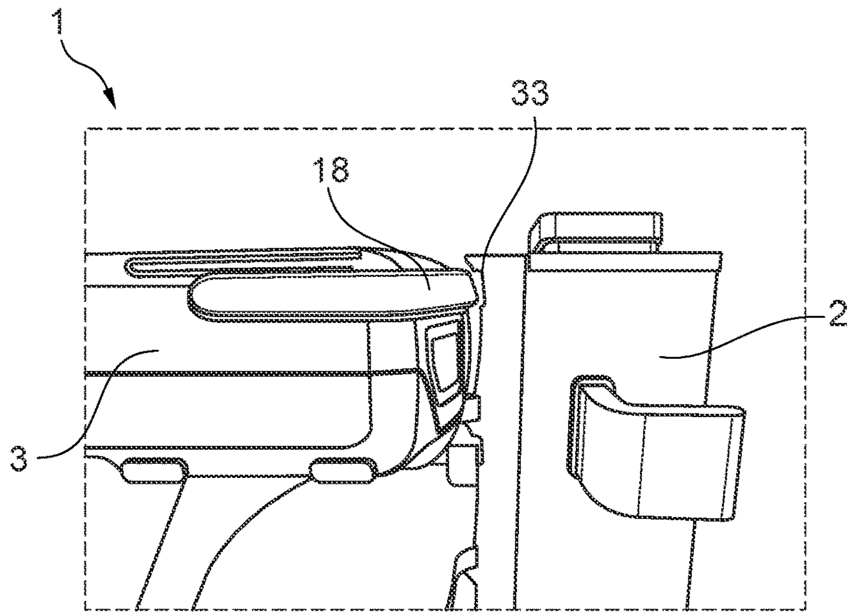
FIG. 10 is a perspective partial view of the supporting or holding system in accordance with the disclosure according to the preferred embodiment.
Figure 11:
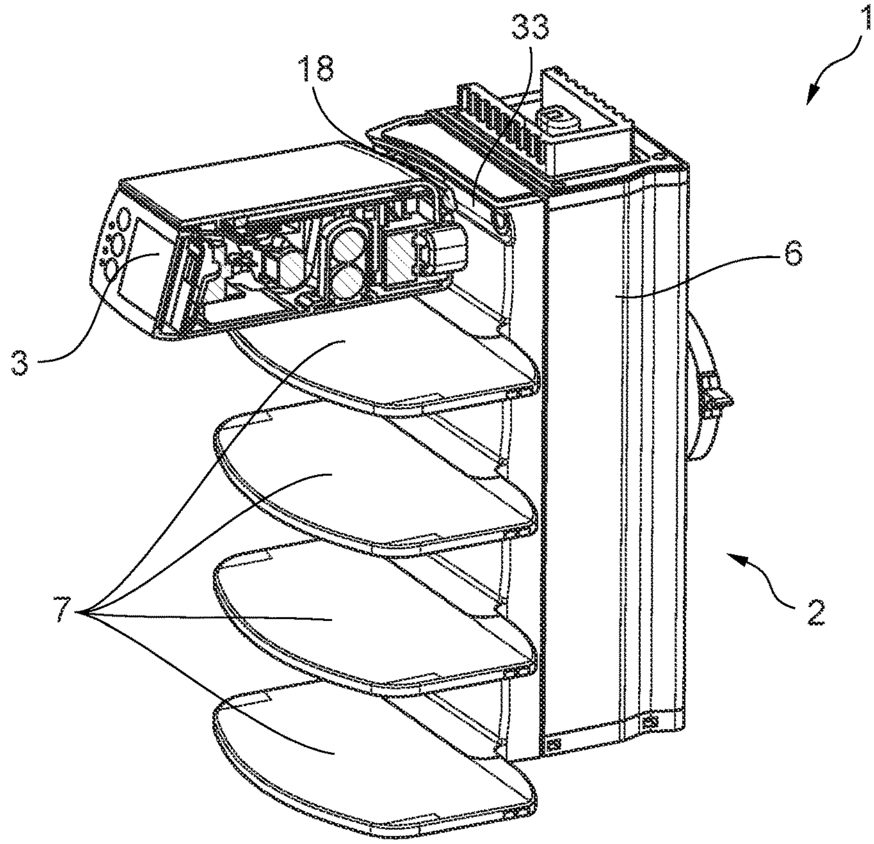
FIG. 11 is a perspective partial sectional view of the supporting or holding system in accordance with the disclosure according to the preferred embodiment.

In FIGS. 10 and 11 the supporting or holding system 1 is illustrated, wherein only one fluid pump 3 is arranged here at the supporting or holding device 2. At the front side of the basic body 6, a recess/set-off/concavity 33 is formed for each tray 7, which extends over the entire width of the basic body 6. As can be recognized especially in FIG. 10, the recess 33 is designed such that the carrying handle 18, when the fluid pump 3 is firmly arranged at the supporting or holding device 2, engages in the recess 33 and/or gets to rest therein. This means that the carrying handle 18 is received in the recess 33. Thus, the distance between the fluid pump 3 and the basic body 6 may be reduced in the coupled state although the carrying handle 18, as mentioned before, projects over the rear side of the fluid pump 3 for better handling.

The present disclosure has been explained above by means of a fluid pump 3 designed as an infusion pump 4. It is to be understood that the carrying handle 18 in accordance with the disclosure may also be arranged at a syringe pump 5 or at any other medical fluid pump 3.

The invention claimed is:

1. A medical fluid pump comprising:

a housing having:

two opposing side faces;

a lid face extending between the two opposing side faces;

a bottom face extending between the two opposing side faces opposite the lid face;

a front face extending between the two opposing side faces and pivotably hinged to the housing;

a rear face extending between the two opposing side faces opposite the front face;

a carrying handle pivotably hinged to the two opposing side faces to rotate relative to the housing, about a swivel axis extending between the two opposing side faces, between a swiveled-out state and a swiveled-in state; and a lock comprising:

a groove body comprising a groove body surface and a first groove extending into the groove body surface in a groove direction along the swivel axis;

a rib facing the groove body and extending in the groove direction along the swivel axis, wherein the rib and the groove body are rotatable relative to one another about the swivel axis upon rotation of the carrying handle between the swiveled-out state and the swiveled-in state; and a spring having a spring bias configured to bias the rib and the groove body together along the swivel axis, and move the rib into the first groove when the carrying handle is in at least one of the swiveled-out state and the swiveled-in state;

wherein a handle portion of the carrying handle is located in a direction of gravity over the lid face when the carrying handle is in the swiveled-out state, and the handle portion is not located in the direction of gravity over the lid face when the carrying handle is in the swiveled-in state.

2. The medical fluid pump according to claim 1, wherein the handle portion projects in the swiveled-in state at least partially beyond a rear face of the housing.

3. The medical fluid pump according to claim 1, further comprising a spring element having a spring force that counteracts a weight of the carrying handle so as to rotate the carrying handle to the swiveled-out state.

4. The medical fluid pump according to claim 1, wherein the groove body and the rib are configured to generate an acoustic signal when the rib moves into the first groove.

5. The medical fluid pump according to claim 1, wherein the groove body comprises a second groove extending into the groove body surface in the groove direction, and the spring is configured to move the rib into the first groove when the carrying handle is in the swiveled-out state, and move the rib into the second groove when the carrying handle is in the swiveled-in state.

6. The medical fluid pump according to claim 5, wherein the first groove extends along a first elongation direction, the second groove extends along a second elongation direction, and the first elongation direction is perpendicular to the second elongation direction.

7. The medical fluid pump according to claim 1, wherein the carrying handle comprises at least one damping element, which rests on the housing in the swiveled-in state.

8. The medical fluid pump according to claim 7, wherein the at least one damping element is a plastic element received in a blind hole of the carrying handle.

9. The medical fluid pump according to claim 1, further comprising a coupling structure for connecting the medical fluid pump directly with a further medical fluid pump, and the carrying handle is adapted to carry the medical fluid pump and said further medical fluid pump when the medical fluid pump is connected with said further medical fluid pump, wherein:

the coupling structure comprises a respective rail located on each of the two opposing side faces and extending in a direction between the front face and the rear face; and the carrying handle straddles the two opposing side faces and is located below the respective rails in the direction of gravity when the carrying handle is in the swiveled-in state.

10. A supporting or holding system comprising:

at least one medical fluid pump according to claim 1; and a supporting or holding device for position-safe holding of the at least one medical fluid pump, the supporting or holding device comprising:

a basic body having a side face; and a plurality of trays projecting from the side face, each of the plurality of trays adapted to hold said at least one medical fluid pump, the basic body defining a carrying handle receiving opening corresponding to each tray, each carrying handle receiving opening adapted to receive the carrying handle of the at least one medical fluid pump, and at least one of the plurality of trays configured to hold at least one medical fluid pump in an operating position.

11. The medical fluid pump according to claim 1, wherein the front face comprises at least one of: a display, a signal light or an operating key.

12. The medical fluid pump according to claim 9, wherein the housing comprises a bottom face opposite the lid face, and the coupling structure comprises rails extending into the two opposing side faces, and skids extending from the bottom face, wherein the skids and the rails define complementary sliding surfaces so as to slidingly connect respective rails of a first medical fluid pump directly with respective skids a second medical fluid pump.

13. The medical fluid pump according to claim 1, wherein the groove body is movable along the swivel axis and the spring is configured to move the groove body towards the rib to thereby move the rib into the first groove when the carrying handle is in the at least one of the swiveled-out state and the swiveled-in state.

14. The medical fluid pump according to claim 13, further comprising a counter plate rotationally fixed to the carrying handle and positioned along the swivel axis, and wherein the spring is positioned along the swivel axis between the counter plate and the groove body and configured to bias the groove body away from the counter plate.

15. The medical fluid pump according to claim 1, wherein the handle portion lies substantially over a center of gravity of the medical fluid pump when the carrying handle is in the swiveled-out state.

16. The medical fluid pump according to claim 1, wherein the groove body is rotationally fixed to the carrying handle, and the rib is rotationally fixed to the housing.

17. The medical fluid pump according to claim 1, wherein the groove body is movable relative to the housing along the swivel axis, and the spring is positioned along the swivel axis between the groove body and an internal surface within the housing and configured to bias the groove body along the swivel axis away from the internal surface within the housing.

18. The medical fluid pump according to claim 1, wherein:

the housing comprises a through-hole at the swivel axis;

the carrying handle comprises a fastening pin extending along the swivel axis, through the through-hole, and into the housing; and the rib extends perpendicular to the fastening pin on opposite sides of the through-hole.

19. The medical fluid pump according to claim 1, wherein the lock is configured such that a force applied to rotate the carrying handle relative to the housing about the swivel axis acts against the spring bias to move the rib out of the first groove and into contact with the groove body surface to permit rotation between the swiveled-out state and the swiveled-in state.

20. The medical fluid pump according to claim 19, wherein the rib and the first groove comprise rounded shapes that are disengageable by the force.

* * * * *